US012680981B2

(12) United States Patent
Kangas et al.

(10) Patent No.: US 12,680,981 B2
(45) Date of Patent: Jul. 14, 2026

(54) ESTIMATION OF COMMINUTION ENERGY CONSUMPTION FOR ROCK COMMINUTION

(71) Applicant: LUMO ANALYTICS LTD, Helsinki (FI)

(72) Inventors: Lasse Kangas, Aalto (FI); Jussi Leveinen, Aalto (FI)

(73) Assignee: LUMO ANALYTICS LTD, Helsinki (FI)

( * ) Notice: Subject to any disclaimer, the term of this patent is extended or adjusted under 35 U.S.C. 154(b) by 243 days.

(21) Appl. No.: 18/041,982

(22) PCT Filed: Sep. 15, 2021

(86) PCT No.: PCT/FI2021/050610
§ 371 (c)(1),
(2) Date: Feb. 16, 2023

(87) PCT Pub. No.: WO2022/058653
PCT Pub. Date: Mar. 24, 2022

(65) Prior Publication Data
US 2023/0314381 A1     Oct. 5, 2023

(30) Foreign Application Priority Data
Sep. 16, 2020    (FI) ...................................... 20205892

(51) Int. Cl.
*G01N 29/04*          (2006.01)
*B23K 26/00*          (2014.01)
(Continued)

(52) U.S. Cl.
CPC ........... *G01N 29/045* (2013.01); *B23K 26/00* (2013.01); *B23K 26/03* (2013.01); *B23K 26/06* (2013.01);
(Continued)

(58) Field of Classification Search
CPC .... B02C 19/18; B23K 26/03; B23K 26/0622; B23K 26/356; B23K 2103/50;
(Continued)

(56) References Cited

U.S. PATENT DOCUMENTS 5,004,166 A * 4/1991 Sellar ...................... B02C 19/18
                                                            241/1
5,131,957 A   7/1992 Epstein et al.
(Continued)

FOREIGN PATENT DOCUMENTS

CA        2287024 A1     4/2001
CA        2574867 A1     1/2006
(Continued)

OTHER PUBLICATIONS

Finnish Patent and Registration Office, Search Report Issued in U.S. Appl. No. 20/205,892, filed Apr. 27, 2021, 2 pages.
ISA European Patent Office, International Search Report Issued in Application No. PCT/FI2021/050610, Feb. 10, 2022, WIPO, 2 pages.

*Primary Examiner* — Peter J Macchiarolo
*Assistant Examiner* — Monica S Young
(74) *Attorney, Agent, or Firm* — McCoy Russell LLP

(57) ABSTRACT

Disclosed is an apparatus and method for facilitating an estimation of comminution energy consumption for rock comminution. The apparatus comprises a pulsed laser source for ablating rock material to generate laser-induced plasma shock waves, a focusing lens system for focusing the pulsed lased source for ablating the rock material and a microphone for capturing the laser-induced plasma shock waves for estimating the comminution energy consumption for the rock material.

15 Claims, 3 Drawing Sheets

(51) Int. Cl.

| | |
|---|---|
| *B23K 26/03* | (2006.01) |
| *B23K 26/06* | (2014.01) |
| *B23K 26/0622* | (2014.01) |
| *B23K 26/356* | (2014.01) |
| *G01N 21/71* | (2006.01) |
| *G01N 29/14* | (2006.01) |
| *G01N 29/24* | (2006.01) |
| *G01N 29/44* | (2006.01) |
| *G01N 29/46* | (2006.01) |
| *G01N 33/24* | (2006.01) |

(52) U.S. Cl.
CPC ........ *B23K 26/0622* (2015.10); *B23K 26/356* (2015.10); *G01N 21/718* (2013.01); *G01N 29/14* (2013.01); *G01N 29/2418* (2013.01); *G01N 29/46* (2013.01); *G01N 33/24* (2013.01); *G01N 29/4445* (2013.01); *G01N 2291/0232* (2013.01)

(58) Field of Classification Search
CPC ............ B23K 26/0665; G01N 29/045; G01N 29/2418; G01N 21/718; G01N 29/14; G01N 29/4445; G01N 29/46; G01N 33/24; G01N 2291/0232; G01H 3/08
USPC ........................................................ 73/12.01
See application file for complete search history.

(56) References Cited

U.S. PATENT DOCUMENTS

| | | | | |
|---|---|---|---|---|
| 10,258,410 | B2 * | 4/2019 | Hiereth ................. | A61B 18/26 |
| 2001/0045416 | A1 | 11/2001 | Sokol et al. | |
| 2006/0102343 | A1 * | 5/2006 | Skinner ............... | B23K 26/082 |
| | | | | 166/57 |
| 2016/0108687 | A1 | 4/2016 | Rapoport | |
| 2018/0272469 | A1 * | 9/2018 | Mariella, Jr. ...... | B23K 26/0622 |
| 2019/0346370 | A1 * | 11/2019 | Harhira ................ | G01N 21/718 |
| 2020/0276593 | A1 | 9/2020 | Mueller et al. | |
| 2022/0022960 | A1 * | 1/2022 | Polejaev ............. | A61B 5/4836 |
| 2024/0329202 | A1 * | 10/2024 | Altshuler .............. | A61B 18/22 |

FOREIGN PATENT DOCUMENTS

| | | | | | |
|---|---|---|---|---|---|
| CN | 104535544 | A | * | 4/2015 | |
| CN | 108844898 | A | | 11/2018 | |
| CN | 109781622 | A | | 5/2019 | |
| CN | 116087016 | A | * | 5/2023 | ............... G01N 3/58 |
| CN | 219871823 | U | * | 10/2023 | |
| CN | 117804390 | A | * | 4/2024 | ............ G01B 17/02 |
| EP | 3456417 | A1 | * | 3/2019 | ......... B02C 17/1805 |
| WO | WO-9423478 | A2 | * | 10/1994 | ............ A61B 18/26 |

* cited by examiner

200

ABLATE ROCK MATERIAL
TO GENERATE
LASER-INDUCED PLASMA SHOCK WAVE

120

CAPTURE LASER-INDUCED PLASMA
SHOCK WAVE FOR ESTIMATING
COMMINUTION ENERGY CONSUMPTION

210

MEASURE DISTANCE TO ROCK MATERIAL
FOR MAINTAINING DISTANCE DURING
REPEATED ABLATION

220

ESTIMATION OF COMMINUTION ENERGY CONSUMPTION FOR ROCK COMMINUTION

CROSS REFERENCE TO RELATED APPLICATIONS

The present application is a U.S. National Phase of International Application No. PCT/FI2021/050610 entitled "APPARATUS FOR AND METHOD OF FACILITATING AN ESTIMATION OF COMMINUTION ENERGY ROCK CONSUMPTION FOR COMMINUTION," and filed on Sep. 15, 2021. International Application No. PCT/FI2021/050610 claims priority to Finnish Patent Application No. 20205892 filed on Sep. 16, 2020. The entire contents of each of the above-listed applications are hereby incorporated by reference for all purposes.

FIELD

The present invention relates to mining and aggregate processing, specifically to rock comminution such as crushing and grinding for obtaining minerals from rock material. In particular, the present invention relates to estimating the energy required for comminution, i.e. reducing the piece-size of the rock material.

BACKGROUND

Comminution is an essential part of ore processing, which usually comprises two phases, crushing and grinding. In ore processing, the purpose of comminution is to liberate the valuable minerals from the multi-mineral matrix by reducing the size of raw ore. Besides achieving liberation of valuable minerals, the particle size is optimized to achieve optimum separation process. The benefits of the optimization include decrease in energy consumption, increased throughput, improved process efficiency and longer lifetime of grinding consumables.

As the comminution processes are highly energy intensive (by one estimate 4% of global electrical energy consumption), the milling energy consumption of different ore types is usually estimated with standard methods like bond ball mill or point load test. These physical tests are time consuming and therefore cannot be used in daily surveillance of processing plant input feed. To make matters more complicated, larger mines are usually mining different locations of the ore deposit simultaneously. Therefore, the raw ore coming to the plant may have different physical properties that affect the comminution properties of the feed. This may lead to under grinding, which decreases the ore intake, or over grinding, which decreases the throughput and the lifetime of grinding consumables while additionally increasing the energy consumption.

Therefore, an automated way to estimate proper process parameters for the incoming ore feed is needed.

Objective

An objective is to alleviate the disadvantages mentioned above.

In particular, it is an objective to facilitate an automated way to estimate comminution energy consumption.

SUMMARY

Herein, "comminution" may refer to crushing and/or grinding. Similarly, "comminution energy consumption"

may refer to crushability and/or grindability. All examples disclosed may be adapted for ore processing, in particular for estimating comminution energy consumption for a comminution circuit of a mineral processing plant. Correspondingly, "rock" and "rock material" may specifically be considered to refer to ore and ore material, for example to an input feed of a comminution circuit. Also herein, "acoustic signal" may be used to indicate the acoustic signal corresponding to one or more shock waves.

In accordance with the present disclosure, it has been found that comminution energy consumption may be estimated by utilizing a measurement of an acoustic signal of laser-induced plasma shock waves from rock material such as an input feed of a comminution circuit. It has been found that an acoustic fingerprint created for a rock material may be associated with the comminution energy consumption of the rock material. This acoustic fingerprint may subsequently be used to identify the comminution energy consumption of any corresponding rock material such as an input feed of a comminution circuit.

A technical solution may comprise an apparatus that creates laser-induced plasmas from rock material and records the laser-induced plasma shock waves (LPSW) associated with the ablation and plasma formation.

According to a first aspect, an apparatus for facilitating an estimation of comminution energy consumption for rock comminution is disclosed. The apparatus comprises a pulsed laser source for ablating rock material to generate laser-induced plasma shock waves. This allows generating miniature explosions on the rock material that convey suitable acoustic information for providing the acoustic fingerprint of the rock material for estimating its comminution energy consumption. The apparatus further comprises a focusing lens system for focusing the pulsed lased source for ablating the rock material allowing the laser pulse to be directed and focused appropriately also during a series of subsequent laser pulses. The apparatus also comprises a microphone for capturing the laser-induced plasma shock waves for estimating the comminution energy consumption for the rock material. The acoustic information for recognizing the acoustic fingerprint of the rock material can thus be recorded and processed accordingly locally and/or remotely.

In an embodiment, the apparatus is a drill core logger, a hand-held rock analyzer, a conveyor-belt rock analyzer or a standoff wall scanner. Different apparatuses allow the LPSW-measurements to be performed using rock material in different stages of mining. One approach is to do the measurements as a part of the core logging that is usually major part of the quality control in active mines. Another approach is to measure hand specimens from stockpiles. In one embodiment, it can be done from the input feed conveyor belt in the processing plant.

In an embodiment, the apparatus comprises one or more distance-to-target measurement units for determining one or more distances to the rock material. This includes determining a distance indicative of the position of the focus for the pulsed laser source with respect to the rock material. Firstly, determining a distance to the rock material for the laser pulse allows the apparatus to maintain a constant focus to the rock material, even during a series of subsequent laser pulses, thereby markedly improving the quality of the acoustic signal obtained from the rock material. For this purpose, the distance between the focus, i.e. the focus point, of the pulsed laser source and the rock material may be maintained constant. The focus may be shifted by repositioning the lens system and/or the laser source. Maintaining the focus constant with respect to the rock material allows the intensity of the acoustic signal to be controlled more carefully as the intensity is dependent on the spot size of the laser pulse at the rock material. This allows reducing bias in the acoustic signal and assuring that ablation occurs with every laser pulse. It is noted that the distance may be also zero, in which case the focus for the pulsed laser source may be maintained at the rock material. Furthermore, determining the distance of the microphone with respect to the rock material allows the microphone to be maintained at constant distance with respect to the rock material for measurement of subsequent shock waves or any changes in the acoustic signal due to a change in the distance computationally corrected. Correspondingly, the acoustic signal may be normalized with respect to the distance between the microphone and the rock material.

In an embodiment, the apparatus is configured to perform a repeated cycle of generating a laser pulse with the pulsed laser source for ablating the rock material, focusing the laser pulse with respect to the rock material, for example at the rock material, with the focusing lens system for generating the one or more laser-induced plasma shock waves, capturing the one or more laser-induced plasma shock waves by the microphone and measuring the distance to the rock material by the distance-to-target measurement system for maintaining the one or more distance to the rock material and/or computationally compensating for any changes in the one or more distances. For this purpose, the apparatus may comprise a controller, which may be configured for causing the cycle to be performed. For example, the controller may be configured to maintain the focus for the pulsed laser source constant with respect to the rock material, for example at the rock material. Additionally or alternatively, it may be configured to maintain the distance of the microphone with respect to the rock material and/or normalizing the acoustic signal with respect to the distance. For maintaining the distances, the controller may be configured for causing any combination of the laser source, the lens system, the microphone and the apparatus as a whole to be repositioned. The order of the actions may be as indicated or different. The cycle may consist of the indicated actions or it may comprise additional actions, including one or more repetitions of said actions. In any case, the cycle allows improving the quality of the acoustic signal obtained from the rock material, which may markedly improve its association with a corresponding acoustic fingerprint. In a further embodiment, the cycle is repeated a plurality of times, for example at least 100 or 1000 times, for a single estimate of comminution energy consumption.

In an embodiment, the capturing frequency of the microphone for capturing the shock waves is larger than the repetition rate of the pulsed laser source for ablating the rock material. This reduces overlap between shock waves generated by subsequent laser pulses. It has further been found that when the capturing frequency is at least ten times larger than the repetition rate, marked improvement in the quality of acoustic signal for estimating the comminution energy consumption may be obtained. In a further embodiment, the capturing frequency of the microphone is at least ten kilohertz. This allows improved capturing of the laser-induced plasma shockwave generation process having a short lifetime as an extended amount of information can be captured for a single ablation process.

In an embodiment, the apparatus is configured to estimate the comminution energy consumption utilizing a machine-learning algorithm for associating acoustic signals corresponding to laser-induced plasma shock waves with the comminution energy consumption for the rock material. A machine-learning algorithm as indicated has been found to provide an efficient way for providing the acoustic fingerprint for the rock material and it may be utilized accordingly.

In an embodiment, the apparatus comprises an optical detector for capturing an optical signal from the ablated rock material for laser-induced breakdown spectroscopy for the rock material. This allows the estimate of the comminution energy consumption to be further improved by inclusion of optical data for determining the estimate, in addition to the acoustic data from the one or more laser-induced plasma shock waves.

According to a second aspect, a comminution circuit comprises the apparatus according to the first aspect or any of its embodiments is disclosed. The apparatus is configured for facilitating an estimation of comminution energy consumption for an input feed of the comminution circuit. For this purpose, the laser source and the microphone can be configured for being directed at the input feed, for example at a conveyor belt of the comminution circuit transporting the input feed. The laser source may be positioned to have a clear view at the input feed for the ablation of the input feed. The microphone may be positioned to have a clear view at the input feed for capturing the shock waves.

According to a third aspect, a method for facilitating an estimation of comminution energy consumption for rock comminution is disclosed. The method comprises ablating rock material by a pulsed laser source to generate one or more laser-induced plasma shock waves and capturing the one or more laser-induced plasma shock waves by a microphone for estimating the comminution energy consumption for the rock material. What is described above in connection of the first and second aspects or any of their embodiments applies also for the third aspect and its embodiments.

In an embodiment, the method is performed at core logging of the rock material or at an input feed conveyor belt of a comminution circuit.

In an embodiment, the method comprises measuring one or more distances to the rock material for maintaining the one or more distances during repeated ablation of the rock material and/or computationally compensating for any changes in the one or more distances. The one or more distances may include the distance between the focus for the pulsed laser source, as focused by the lens system, and the rock material and/or the distance between the microphone and the rock material. In the first case, the distance may be also zero so that the focus for the pulsed laser source is at the rock material.

In an embodiment, the method comprises a repeated cycle of generating a laser pulse for ablating the rock material, focusing the laser pulse with respect to the rock material for generating the one or more laser-induced plasma shock waves, capturing the one or more laser-induced plasma shock waves and measuring the distance to the rock material for maintaining the one or more distances to the rock material and/or computationally compensating for any changes in the one or more distances.

In an embodiment, the method comprises receiving a signal corresponding the one or more laser-induced plasma shock waves captured by the microphone in time domain and transforming the signal into frequency domain for estimating the comminution energy requirement. For some applications, this has been found to markedly improve the quality of the signal for estimating the comminution energy consumption. The transformation may be performed as a discrete Fourier transform, for example as a fast Fourier transform for ensuring computational efficiency.

In an embodiment, the method comprises estimating the comminution energy consumption utilizing a machine-learning algorithm for associating acoustic signals corresponding to laser-induced plasma shock waves with the comminution energy consumption for the rock material.

In an embodiment, the method comprises capturing an optical signal from the ablated rock material for laser-induced breakdown spectroscopy for the rock material. This optical signal may then be used together with the acoustic signal from the one or more laser-induced plasma shock waves for estimating the comminution energy consumption.

According to a fourth aspect, a computer program product comprises instructions which, when the computer program product is executed by a computer, cause the computer to associate acoustic signals corresponding to laser-induced plasma shock waves with the comminution energy consumption for the rock material.

In an embodiment, a machine-learning algorithm is utilized for associating the acoustic signals with the comminution energy consumption.

In an embodiment, the computer program product is a program product for controlling a comminution circuit.

According to a fifth aspect, acoustic signals corresponding to laser-induced plasma shock waves are used to estimate comminution energy consumption of a rock material.

In an embodiment, the comminution energy consumption is estimated for a rock material corresponding to an input or output feed of a comminution circuit. The feed may be conveyed on a conveyor belt of the comminution circuit.

In accordance with the present disclosure, the estimate for the comminution energy consumption for the rock material may be provided by generating multiple laser-induced plasma shock waves by multiple subsequent laser pulses. The laser pulse properties may be maintained substantially constant. This includes peak energy, duration, optical divergence, wavelength and spatial and temporal energy distribution of the laser pulse. Short laser pulses may be used, for example less than 100 nanoseconds, which has been found to reduce interaction with the expanding plasma and the incoming excitation laser pulse.

It has further been found that the present disclosure may be utilized at least substantially non-invasively for the rock material. The acoustic fingerprint of the rock material can therefore be maintained independent of the running number of the laser pulse, i.e. the acoustic fingerprint corresponding the first pulse may be substantially the same as that of any latter pulse. In principle, it is therefore enough to obtain a single laser-induced plasma shock wave from a single point on the surface of the rock material to estimate the corresponding comminution energy consumption. Multiple laser pulses may still be generated for obtaining multiple substantially identical laser-induced plasma shock waves at different points on the surface of the rock material and/or for reducing the statistical variation of the acoustic signal corresponding to the single point. However, in accordance with the present disclosure, the laser pulses utilized may be substantially non-invasive for the rock material, i.e. they may be generated in such a manner that the acoustic response, i.e. the acoustic fingerprint, of the rock material is maintained constant during generation of the laser pulses. There is therefore no need, for example, to excavate the rock material for changing the acoustic response as a function of the running number of the laser pulse. The laser pulses may be generated accordingly, for example by limiting the energy of each single laser pulse and/or the total energy of multiple pulses generated for estimation of the comminution energy consumption.

An accurate knowledge of the processed (crushed, grinded, drilled, etc.) material enables the optimization of the processes and therefore decreases consumption of energy, wearing parts and time, particularly when operating a comminution circuit. As this technique can also be used remotely (for example up to tens of meters), the rapid classification of ores and waste rocks from feasible working distances can also improve occupational safety in mines. The disclosure may also be used to allow selective mining and the optimization of excavation and mineral processing. This increases the economic efficiency and environmental performance of mining companies and quarries. This method can also be implemented for recycling processes, waste management and in concrete technologies.

It is to be understood that the aspects and embodiments described above may be used in any combination with each other. Several of the aspects and embodiments may be combined together to form a further embodiment of the invention.

BRIEF DESCRIPTION OF THE DRAWINGS

The accompanying drawings, which are included to provide a further understanding and constitute a part of this specification, illustrate examples and together with the description help to explain the principles of the disclosure. In the drawings.

Like references are used to designate equivalent or at least functionally equivalent parts in the accompanying drawings.

DETAILED DESCRIPTION

The detailed description provided below in connection with the appended drawings is intended as a description of examples and is not intended to represent the only forms in which the example may be constructed or utilized. However, the same or equivalent functions and structures may be accomplished by different examples.

Figure 1:
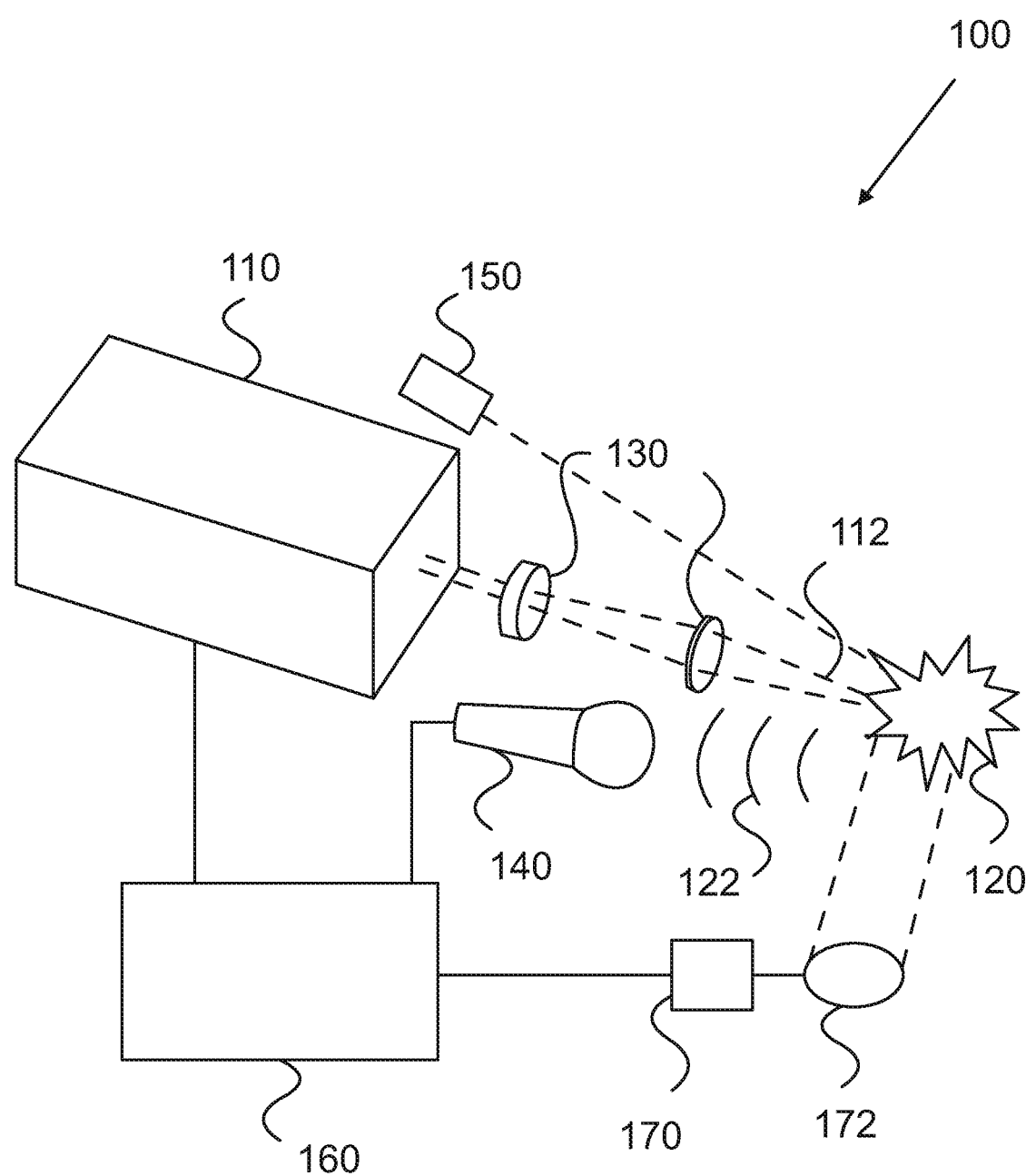
FIG. 1 illustrates an apparatus according to an example.

FIG. 1 schematically shows an example of an apparatus 100 for facilitating an estimation of comminution energy consumption for rock comminution.

The apparatus 100 comprises a pulsed laser source 110 for ablating rock material to generate laser-induced plasma shock waves 122. The laser source can be configured to generate laser pulses 112 with a repetition rate, which may be constant in time, for example. In addition, the apparatus comprises a lens system 130, which may comprise one or more lens for focusing the laser pulses. The lens system may also be configured to reduce beam divergence for the laser pulses. With the lens system, a laser pulse from the laser source can be focused onto a small area near or at the surface of rock material so that upon contact it ablates 120 a small amount of material, for example in the range of nanograms to picograms, generating a plasma plume with elevated temperature. This ablation may be considered as a miniature explosion on the surface of the rock material, which thereby creates an acoustic signal in the form of one or more laser-induced plasma shock waves. For ablation, the laser source has a peak power exceeding the ablation threshold of the rock material, for example in units $GW/cm^2$. In an embodiment, each laser pulse has a length smaller than a microsecond. For example, a pulse length of 1-100 nanoseconds has been found to provide particularly applicable results but in some embodiments the pulse length may be even smaller, for example in the pico- or femtosecond scale, whereas in some embodiments it may be larger, for example in the microsecond scale.

The apparatus 100 comprises a microphone 140 for capturing the laser-induced plasma shock waves 122, i.e. the acoustic signal, from the ablation 120. The microphone has a capturing frequency, which may be larger than the repetition rate of the laser source 110, in particular ten times as large or larger. This may reduce overlap between shock waves generated by subsequent ablations. The capturing frequency of the microphone may be tens of thousands of hertz or more, for example 40 kHz or more, allowing detailed recording of the ablation process having a short lifetime. The microphone may be maintained active for an extended period of time for capturing multiple shock waves, for example a minimum of 100-1000 shock waves. This allows the microphone to be constantly reactive for the shock waves, which may be generated at very short time intervals.

The acoustic signal 122 captured by the microphone 140 is used for estimating the comminution energy consumption for the rock material. This may be done by comparing the acoustic signal to an acoustic fingerprint of one or more rock materials. By measuring and processing multiple points from samples of rock material with known properties, an acoustic fingerprint of the corresponding rock material can be captured. These fingerprints can then be used to estimate the comminution energy consumption of unknown samples, which may be coming from the same domain. For example, principal component analysis and/or machine learning algorithms may be used for the estimation. The estimated comminution energy consumption may be expressed by a scalar value or, in some cases, multiple scalar values, for example when comminution energy consumption for an extended sample of rock material is estimated. In addition, one or more mechanical parameters for the rock material may be estimated, for example uniaxial compressive strength (UCS) and/or uniaxial tensile strength (UTS). Alternatively or additionally, any processing parameters related to any combination of crushability, grindability, drillability and excavation, for example, blasting, may be estimated. The acoustic signal may be recorded and/or transmitted for analysis. For these purposes, the apparatus 100 may comprise a recorder and/or transmitter. Alternatively or additionally, the apparatus may comprise a controller 160, which may also function as an analyzer. Naturally, the apparatus may also comprise a dedicated analyzer. The controller and/or the analyzer, or the controller-analyzer, may comprise one or more processors. It may also comprise one or more memories comprising computer program code which, when executed by the one or more processors, can cause any of the actions described in this disclosure to be performed.

The apparatus 100 may additionally comprise one or more distance-to-target measurement units for determining one or more distances to the rock material. These units may be positioned at the lens system 130 and/or the microphone 140 for determining distance to the rock material from the lens system for providing the laser pulse 112 to the rock material and/or from the microphone for capturing the shock waves 122 from the rock material. The distance-to-target measurement unit may be an optical measurement unit, for example a laser-based unit for distance-to-target measurement. In particular, a distance-to-target measurement unit may be configured for determining a distance for indicating the position of the focus of the pulsed laser source, and thereby that of the laser pulse, with respect to the rock material. This may be used, for example by the controller 160 for maintaining the focus for the laser source, and thereby that of the laser pulse, constant with respect to the rock material, for example at the rock material. On the other hand, the controller and/or the analyzer may be configured for normalizing the acoustic signal with respect to the distance between the microphone and the rock material. This may be performed by utilizing the fact that the intensity of the acoustic signal is inversely proportional to the distance squared. Measuring the distance of the microphone with respect to the rock material, by a distance-to-target measurement unit thereby allows the acoustic signal intensity to be normalized by a distance correction.

For the ablation 120, a pulsed laser source 110 and focusing lens system 130 suitable for laser-induced breakdown spectroscopy may be used. Since the ablation can also generate an optical signal 124, the apparatus 100 may also comprise an optical detector 170 for capturing the optical signal from the ablated rock material. The optical signal can be used for laser-induced breakdown spectroscopy for the rock material and thereby can be used to supplement the information obtained from the acoustic signal 122. The apparatus may comprise an additional optical system 172, such as a lens system, for collecting the optical signal from the ablated rock material for the optical detector. As the analyzer is configured to analyze the acoustic signal it may also be configured to analyze the optical signal. Similarly, the optical signal may be recorded and/or transmitted for analysis by the recorder and/or transmitter, respectively. The apparatus may comprise one or more spectrometers for measuring spectral components of the optical signal. These may include one or more of the following in any combination: an ultra-violet light spectrometer, a near-infrared spectrometer and a visible light spectrometer.

A modular structure for the apparatus 100 (e.g. laser source, lens system, microphone, optical detector) enables tailoring the apparatus in accordance with application requirements. Cost-efficient off-the-shelf components may also be used. The components may be compact in size allowing also the apparatus to be made compact.

The apparatus 100 may comprise a measurement head, which can provide a common support for any combination of the abovementioned components. The measurement head comprises the laser source 110 and, optionally the microphone 140, which may also be positioned separate from the measurement head. The respective positioning of the laser source and the microphone may be fixed or movable. The measurement head may also comprise the lens system 130 and/or the distance-to-target measurement unit 150. The measurement head may comprise the optical detector 170 and, optionally, the additional optical system 172. The lens system and the additional optical system may be positioned adjacent to each other so that the laser pulse is provided from the apparatus at substantially the same location as where the optical signal is received from the rock material. Attaching components on a single measurement head allows their respective positioning to be carefully controlled as they share a common support.

The apparatus 100 may comprise one or more actuators for repositioning the apparatus for maintaining the one or more distances to the rock material. The actuators may comprise one or more linear and/or rotary actuators. The one or more actuators allow the distance of the focus and/or the microphone 140 with respect to the rock material to be maintained constant or substantially constant, even during measurement for subsequent laser pulses 112, the number of which may exceed 1000. For this purpose, the actuators may be configured for repositioning, at least, the lens system 130 and/or the microphone. In one example, this may be accomplished by repositioning the whole measurement head for maintaining the position of the measurement head constant with respect to the rock material. On the other hand, the actuators may also be configured for repositioning the lens system and/or the microphone with respect to the laser source, or the measurement head. Repositioning the apparatus may comprise separately or simultaneously repositioning the lens system 130 for providing the laser pulse 112 to the rock material and/or the microphone for capturing the shock waves 122 from the rock material. For example, when the measurement head comprises both the lens system and the microphone, they can both be repositioned simultaneously in a straightforward manner with the same one or more actuators. Naturally, microphone may also be coupled to the measurement head in a manner allowing it to be repositioned with the one or more actuators for repositioning the measurement head.

The apparatus 100 may be part of a comminution circuit, for example a conveyor-belt rock analyzer therein. In specific embodiments, the apparatus is drill core logger, a hand-held rock analyzer, a conveyor-belt rock analyzer or a standoff wall scanner. As an example, the standoff wall scanner may produce point cloud data of scanned rock material and associate each measurement point with attribute values identifying the material or, in particular, its comminution energy consumption. The standoff wall scanner may be configured for scanning a rock wall for estimating the comminution energy consumption for the rock material of the wall. The standoff wall scanner may be configured for transportation within a mine and for scanning the walls and/or ceiling of the mine for estimating the comminution energy consumption of the rock material therein. The scanner may be used both for underground mines and for surface mines.

The apparatus 100 may be configured to automatically perform measurements for estimating comminution energy consumption for rock comminution, for example as a conveyor-belt rock analyzer. The apparatus may be configured to determine the comminution energy consumption and, optionally, to use and/or transmit the determined comminution energy consumption for controlling the comminution process. The apparatus may comprise an auto-focus for automatically focusing the laser pulse 112 with respect to the rock material, for example at the rock material.

Figure 2:
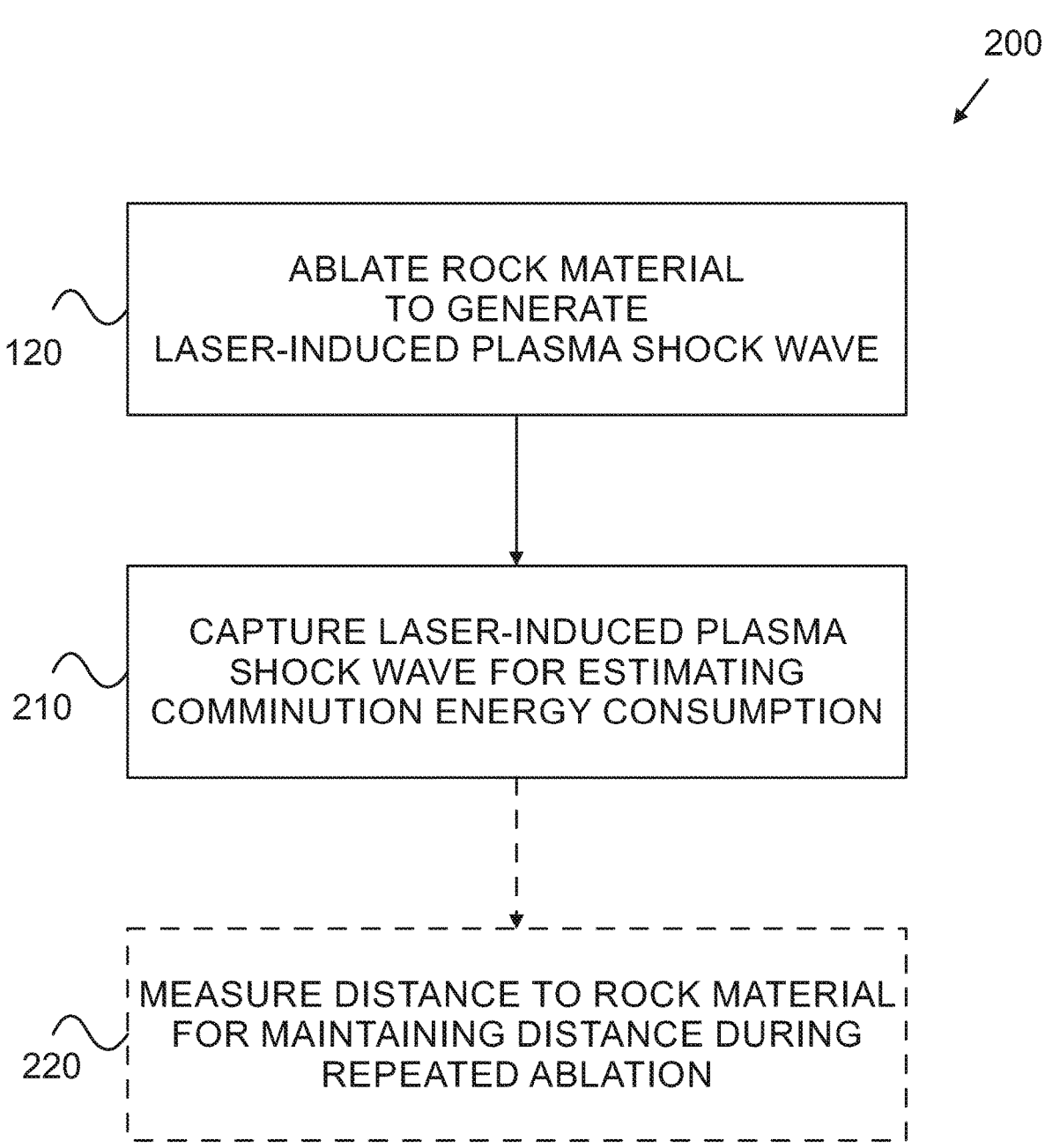
FIG. 2 illustrates a method according to an example.

FIG. 2 shows an example of a method 200 for facilitating an estimation of comminution energy consumption for rock comminution, which may be performed by the apparatus described above. The method comprises ablating 120 rock material by a pulsed laser source to generate one or more laser-induced plasma shock waves and capturing 210 the one or more laser-induced plasma shock waves by a microphone for estimating the comminution energy consumption for the rock material. Any features described in conjunction of the apparatus are applicable for the method and vice versa.

The method may additionally comprise measuring 220 distance to the rock material for maintaining the distance during repeated ablation 120 of the rock material. This may be performed before and/or after the ablation.

Figure 3:
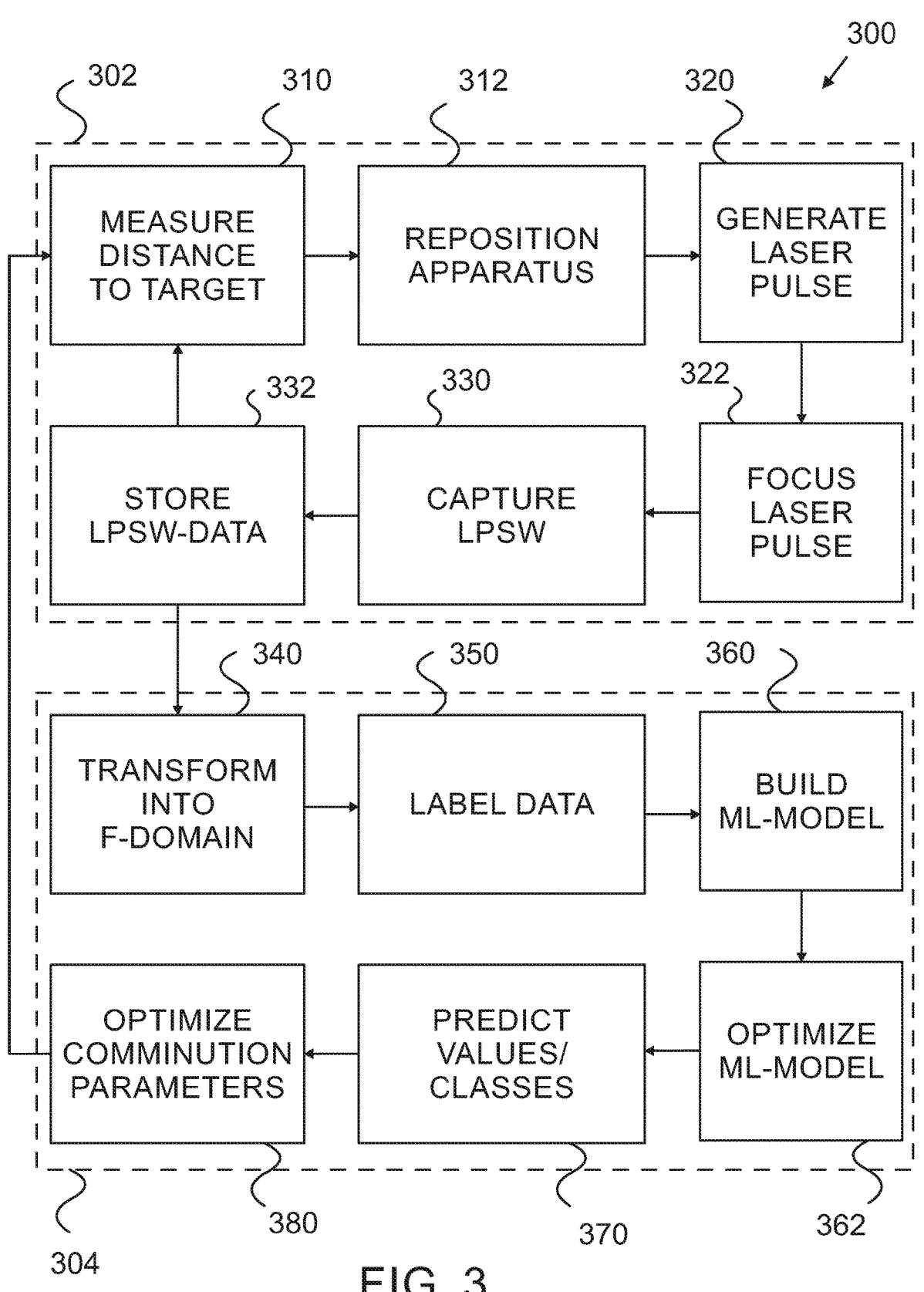
FIG. 3 illustrates a method according to another example.

FIG. 3 shows an example of a method 300 which, in addition to the features described in the context of FIG. 2, comprises one or more additional features. These additional features may be provided also for the apparatus 100 described above, in which case the controller 160 and/or the analyzer may be configured for causing them to be performed.

An example of an additional feature is a repeated cycle of operation for facilitating the estimation of comminution energy consumption for rock comminution. The repeated cycle comprises a repeated measurement cycle 302, which comprises generating 320 the laser pulse 112 for ablating 120 the rock material and focusing 322 the laser pulse with respect to the rock material for generating one or more laser-induced plasma shock waves 122. These may be performed by the pulsed laser source 110 and the lens system 130, as described above. The repeated measurement cycle also comprises capturing 330 the one or more laser-induced plasma shock waves, which may be performed by the microphone 140, as described above.

The acoustic signal corresponding to the one or more laser-induced plasma shock waves 122 may be stored 332 for analysis, for example by the recorder. The repeated measurement cycle 302 may further comprise measuring 310 a distance to the target, i.e. the rock material, for maintaining the distance to the target, including maintaining the focus of the laser pulse 112 with respect to the target, for example at the target. This may be performed by the one or more distance-to-target measurement units 150. Based on one or more measurements of the distance-to-target measurement unit(s), the apparatus 100 may be repositioned 312 to maintain the distance, for example by repositioning the measurement head, or the lens system 130, for providing the laser pulse to the target and/or the microphone 140 for receiving the shock waves from the target. This may be performed by the one or more actuators. In addition, the distance of the microphone with respect to the target may be measured, for example by a distance-to-target measurement unit, for normalizing the acoustic signal with respect to the distance.

The actions pertaining to maintaining the distance 310, 312 and ablating the rock material for measurement 320, 322, 330, 332 may be performed independently from each other and/or in any order with respect to each other. The same holds for data analysis 304, including the optional normalization of the acoustic signal, which provides another example of additional features as indicated above. As indicated, also these features may be performed by the controller 160 and/or the analyzer. The features may be performed locally and/or remotely.

As an additional feature, a signal corresponding the one or more laser-induced plasma shock waves captured by the microphone may be received in time domain and transformed 340 into frequency domain for estimating the comminution energy consumption. In order to examine the frequency distribution of the acoustic signal, a discrete Fourier transform may be performed done to the signal. To ensure computational efficiency, a fast Fourier transform may be calculated.

As another additional feature, which may be used in conjunction or independently from the previous ones, the comminution energy consumption may be estimated utilizing a machine-learning algorithm. This corresponds to the specific example illustrated for data analysis 304 in FIG. 3. In this case, the machine-learning algorithm specifically associates acoustic signals corresponding to laser-induced plasma shock waves with the comminution energy consumption for the rock material. The association may be facilitated by acoustic signal pretreatment and/or classification/regression. A regression or classification algorithm may be taught to learn the specific acoustic fingerprint of rock material with given comminution energy consumption.

The machine-learning algorithm may be supervised, semi-supervised or unsupervised. With the supervised approach, representative samples are taken and the acoustic (LPSW-) signal of the samples is measured as described above. Here, the samples may be taken from different parts of a mine or, in particular, from all relevant parts of the mine. After the measurements, the samples are tested with a standard method (e.g. Bond ball mill, drop weight test, point load test . . . ) that is suitable for the comminution circuit that is used in the processing plant. The LPSW data may then be processed by being labeled 350 with the known values or classes from the standard test. The labeled data may be divided into training, validation and test data, each of which may consist of one or more data sets. A machine-learning model for the machine learning algorithm may be built 360 by entering the training data into the machine-learning algorithm. Using the validation data, the parameters of the algorithm may be optimized 362. The accuracy and precision of the machine-learning model may be evaluated with the independent test data. This approach requires relatively large initial contribution of data, which may be obtained from the mine, but the running cost of the system may be markedly reduced.

With the semi-supervised approach, the above examples are modified in that the data may be collected only from certain areas of the mine and the model is updated until it converges. The data for updating the model comes from observing how the algorithm performs and linking that knowledge with the measured acoustic fingerprint of one or more types of rock material. For this purpose, the input and output flows and the running parameters of a processing plant may be observed, for example. This approach may be used to balance both the initial costs and the running costs, whereby the latter may be increased as it takes some time to optimize the circuit.

With the unsupervised approach, the above examples for supervised approach may be modified in that the approach does not need any labeled data or standard comminution test but instead it may optimize the process learning from the actual operation of the algorithm, for example from the input/output feed of a processing plant. The initial costs of this model may be markedly reduced, but it may take longer to converge and the running cost stay higher for longer period.

In all cases, a machine-learning algorithm is used to predict 370 values and/or classes for rock material. Here, these may correspond to associating acoustic signals corresponding to laser-induced plasma shock waves with the comminution energy consumption for the rock material. The machine-learning algorithm may comprise or consist of a deep neural network algorithm, a linear discriminant analysis algorithm or a Gaussian process regression algorithm, for example. The input information of the machine-learning algorithm comprises the acoustic signal but it may be supplemented by the optical signal as described above. Correspondingly, associating acoustic signals as described above may correspond to associating acoustic signals and optical signals corresponding to laser-induced plasma shock waves with the comminution energy consumption for the rock material. A combined acoustic and optical fingerprint for the rock material may thereby be utilized, wherever the use of an acoustic fingerprint is indicated in this disclosure. Naturally, a solely acoustic fingerprint may also be used.

Regardless of whether a machine-learning algorithm is utilized in the estimation, the estimated comminution energy consumption may be utilized for optimizing 380 comminution parameters. These parameters may include one or more operating parameters of a crushing and/or grinding circuit, for example one or more parameters indicating the amount of crushing and/or grinding performed on the rock material. The estimated comminution energy consumption may be used for real-time operation of a comminution circuit. It may be used as feedback information also for the measurement cycle 302.

The apparatus 100 and method 200 disclosed herein may be used, for example, to monitor input and/or output feed of a comminution circuit for estimating comminution energy consumption for rock comminution entering and/or leaving the comminution circuit. This may be performed automatically. The monitoring may be performed, for example, at an input and/or output feed conveyor belt of the comminution circuit. The estimated comminution energy comminution may be used as an input to a controller of the comminution circuit for controlling the comminution circuit, for example for determining the amount and/or intensity of comminution performed at the circuit. The comminution circuit may comprise or consist of a crushing and/or a grinding circuit. Monitoring may be performed separately for the input feed of the crushing circuit and the input feed of the grinding circuit. The same applies for the corresponding output feeds. A comminution circuit may therefore comprise two or more apparatuses as disclosed configured for monitoring two or more feeds, such as input and/or output feeds, of the comminution circuit. The apparatus and method can be used on-line, i.e. during the operation of the comminution circuit.

The apparatus as described above may be implemented in hardware or in any combination of software, hardware and application logic. The application logic, software or instruction set may be maintained on any one of various conventional computer-readable media. A "computer-readable medium" may be any media or means that can contain, store, communicate, propagate or transport the instructions for use by or in connection with an instruction execution system, apparatus, or device, such as a computer. A computer-readable medium may comprise a computer-readable storage medium that may be any media or means that can contain or store the instructions for use by or in connection with an instruction execution system, apparatus, or device, such as a computer. The examples can store information relating to various processes described herein. This information can be stored in one or more memories, such as a hard disk, optical disk, magneto-optical disk, RAM, and the like. One or more databases can store the information used to implement the embodiments. The databases can be organized using data structures (e.g., records, tables, arrays, fields, graphs, trees, lists, and the like) included in one or more memories or storage devices listed herein. The databases may be located on one or more devices comprising local and/or remote devices such as servers. The processes described with respect to the embodiments can include appropriate data structures for storing data collected and/or generated by the processes of the devices and subsystems of the embodiments in one or more databases.

All or a portion of the embodiments can be implemented using one or more general purpose processors, microprocessors, digital signal processors, micro-controllers, and the like, programmed according to the teachings of the embodiments, as will be appreciated by those skilled in the computer and/or software art(s). Appropriate software can be readily prepared by programmers of ordinary skill based on the teachings of the embodiments, as will be appreciated by those skilled in the software art. In addition, the embodiments can be implemented by the preparation of application-specific integrated circuits or by interconnecting an appropriate network of conventional component circuits, as will be appreciated by those skilled in the electrical art(s). Thus, the embodiments are not limited to any specific combination of hardware and/or software.

The different functions discussed herein may be performed in a different order and/or concurrently with each other.

Any range or device value given herein may be extended or altered without losing the effect sought, unless indicated otherwise. Also, any example may be combined with another example unless explicitly disallowed.

Although the subject matter has been described in language specific to structural features and/or acts, it is to be understood that the subject matter defined in the appended claims is not necessarily limited to the specific features or acts described above. Rather, the specific features and acts described above are disclosed as examples of implementing the claims and other equivalent features and acts are intended to be within the scope of the claims.

It will be understood that the benefits and advantages described above may relate to one embodiment or may relate to several embodiments. The embodiments are not limited to those that solve any or all of the stated problems or those that have any or all of the stated benefits and advantages. It will further be understood that reference to 'an' item may refer to one or more of those items.

The term 'comprising' is used herein to mean including the method, blocks or elements identified, but that such blocks or elements do not comprise an exclusive list and a method or apparatus may contain additional blocks or elements.

Although the invention has been the described in conjunction with a certain type of apparatus and/or method, it should be understood that the invention is not limited to any certain type of apparatus and/or method. While the present inventions have been described in connection with a number of examples, embodiments and implementations, the present inventions are not so limited, but rather cover various modifications, and equivalent arrangements, which fall within the purview of the claims. Although various examples have been described above with a certain degree of particularity, or with reference to one or more individual embodiments, those skilled in the art could make numerous alterations to the disclosed examples without departing from the scope of this specification.

The invention claimed is:

1. An apparatus for facilitating an estimation of comminution energy consumption for rock comminution, the apparatus comprising:
   a pulsed laser source for ablating rock material to generate laser-induced plasma shock waves;
   a focusing lens system for focusing the pulsed lased source for ablating the rock material;
   a microphone for capturing the laser-induced plasma shock waves for estimating the comminution energy consumption for the rock material; and
   a processor for comparing an acoustic signal corresponding to the laser-induced plasma shock waves to an acoustic fingerprint of one or more rock materials.

2. The apparatus according to claim 1, wherein the apparatus is a drill core logger, a hand-held rock analyzer, a conveyor-belt rock analyzer or a standoff wall scanner.

3. The apparatus according to claim 1, comprising a distance-to-target measurement unit for determining a distance to the rock material.

4. The apparatus according to claim 3, configured to perform a repeated cycle of generating a laser pulse with the pulsed laser source for ablating the rock material, focusing the laser pulse with respect to the rock material with the focusing lens system for generating the one or more laser-induced plasma shock waves, capturing the one or more laser-induced plasma shock waves by the microphone and measuring the distance to the rock material by the distance-to-target measurement system for maintaining the distance to the rock material and/or computationally compensating for any changes in the distance.

5. The apparatus according to claim 1, wherein the capturing frequency of the microphone for capturing the shock waves is larger than the repetition rate of the pulsed laser source for ablating the rock material.

6. The apparatus according to claim 1, configured to estimate the comminution energy consumption utilizing a machine-learning algorithm for associating acoustic signals corresponding to laser-induced plasma shock waves with the comminution energy consumption for the rock material.

7. The apparatus according to claim 1, comprising an optical detector for capturing an optical signal from the ablated rock material for laser-induced breakdown spectroscopy for the rock material.

8. A comminution circuit comprising the apparatus according to claim 1, wherein the apparatus configured for facilitating an estimation of comminution energy consumption for an input feed of the comminution circuit.

9. A method for facilitating an estimation of comminution energy consumption for rock comminution, the method comprising:
   ablating rock material by a pulsed laser source to generate one or more laser-induced plasma shock waves;
   capturing the one or more laser-induced plasma shock waves by a microphone for estimating the comminution energy consumption for the rock material; and
   comparing an acoustic signal corresponding to the laser-induced plasma shock waves to an acoustic fingerprint of one or more rock materials.

10. The method according to claim 9, performed at core logging of the rock material or at an input feed conveyor belt of a comminution circuit.

11. The method according to claim 9, comprising measuring a distance to the rock material for maintaining the distance and/or computationally compensating for any changes in the distance during repeated ablation of the rock material.

12. The method according to claim 11, comprising a repeated cycle of generating a laser pulse for ablating the rock material, focusing the laser pulse with respect to the rock material for generating the one or more laser-induced plasma shock waves, capturing the one or more laser-induced plasma shock waves and measuring the distance to the rock material for maintaining the distance to the rock material and/or computationally compensating for any changes in the distance.

13. The method according to claim 9, comprising receiving a signal corresponding the one or more laser-induced plasma shock waves captured by the microphone in time domain and transforming the signal into frequency domain for estimating the comminution energy consumption.

14. The method according to claim 9, comprising estimating the comminution energy consumption utilizing a machine-learning algorithm for associating acoustic signals corresponding to laser-induced plasma shock waves with the comminution energy consumption for the rock material.

15. The method according to claim 9, comprising capturing an optical signal from the ablated rock material for laser-induced breakdown spectroscopy for the rock material.

* * * * *